(12) United States Patent
Poehlmann et al.

(10) Patent No.: US 9,353,369 B2
(45) Date of Patent: May 31, 2016

(54) BIOLOGICALLY ACTIVE MOLECULES FOR INFLUENCING VIRUS-, BACTERIA-, PARASITE-INFECTED CELLS AND/OR TUMOR CELLS AND METHOD FOR THE USE THEREOF

(75) Inventors: Tobias Poehlmann, Zwickau (DE); Rolf Guenther, Hamburg (DE)

(73) Assignee: Universitaetsklinikum Jena, Jena (DE)

( * ) Notice: Subject to any disclaimer, the term of this patent is extended or adjusted under 35 U.S.C. 154(b) by 460 days.

(21) Appl. No.: 13/522,411

(22) PCT Filed: Jan. 11, 2011

(86) PCT No.: PCT/DE2011/000024
§ 371 (c)(1),
(2), (4) Date: Oct. 10, 2012

(87) PCT Pub. No.: WO2011/085720
PCT Pub. Date: Jul. 21, 2011

(65) Prior Publication Data
US 2013/0196432 A1    Aug. 1, 2013

(30) Foreign Application Priority Data
Jan. 14, 2010  (DE) .................. 10 2010 004 957

(51) Int. Cl.
*A61K 48/00*  (2006.01)
*C12N 15/11*  (2006.01)
(Continued)

(52) U.S. Cl.
CPC .......... *C12N 15/113* (2013.01); *A61K 31/7088* (2013.01); *A61K 45/06* (2013.01); *A61K 47/48246* (2013.01); *A61K 47/48346* (2013.01);
(Continued)

(58) Field of Classification Search
USPC .......................................... 536/24.5
See application file for complete search history.

(56) References Cited

U.S. PATENT DOCUMENTS

| 5,196,438 A | 3/1993 | Martin et al. |
| 5,413,999 A | 5/1995 | Vacca et al. |

(Continued)

FOREIGN PATENT DOCUMENTS

| EP | 0 691 345 | 1/1996 |
| JP | 2006-223173 | 8/2006 |

(Continued)

OTHER PUBLICATIONS

Makoto Hayakari et al., "A Rapid and Simple Spectrophotometric Assay of Angiotensin-Converting Enzyme", Analytical Biochemistry 84, pp. 361-369 (1978).

(Continued)

*Primary Examiner* — Terra Cotta Gibbs
(74) *Attorney, Agent, or Firm* — Jordan and Hamburg LLP

(57) ABSTRACT

The aim of the invention is to effectively inhibit virus-, bacteria-, or parasite-infected cells and tumor cells in a targeted manner, even in the case of mutations. According to the invention, biologically active molecules are administered, said biologically active molecules including at least one protease inhibitor for at least one specific target protease of the virus-, bacteria-, or parasite-infected cells and/or tumor cells and at least one peptide-inhibited siRNA, PNA or RNA, the peptide bond of which is broken by the at least one target protease for the purpose of activating the peptide-inhibited siRNA, PNA or RNA. The molecules are used, for example, to influence the gene expression of diseased and infected organs or cells.

9 Claims, 2 Drawing Sheets

(51) Int. Cl.
*C07H 21/02* (2006.01)
*C07H 21/04* (2006.01)
*C12N 15/113* (2010.01)
*A61K 31/7088* (2006.01)
*A61K 45/06* (2006.01)
*A61K 47/48* (2006.01)
*B82Y 5/00* (2011.01)

(52) U.S. Cl.
CPC ............ *B82Y 5/00* (2013.01); *C12N 15/111* (2013.01); *C12N 2310/14* (2013.01); *C12N 2310/3513* (2013.01); *C12N 2320/31* (2013.01); *C12N 2320/50* (2013.01)

(56) References Cited

U.S. PATENT DOCUMENTS

| | | |
|---|---|---|
| 5,484,926 A | 1/1996 | Dressman et al. |
| 5,541,206 A | 7/1996 | Kempf et al. |
| 5,585,397 A | 12/1996 | Tung et al. |
| 5,898,031 A | 4/1999 | Crooke |
| 6,107,094 A | 8/2000 | Crooke |
| 6,506,559 B1 | 1/2003 | Fire et al. |
| 7,056,704 B2 | 6/2006 | Tuschl et al. |

FOREIGN PATENT DOCUMENTS

| | | |
|---|---|---|
| WO | WO-03/097616 | 11/2003 |
| WO | WO-2008/098569 | 8/2008 |

OTHER PUBLICATIONS

S. Shah et al., "Tolerance of RNA interference toward modifications of the 5' antisense phosphate of small interfering RNA", Oligonucleotides 2007 Spring 17 (1) pp. 35-43 Abstract.

BIOLOGICALLY ACTIVE MOLECULES FOR INFLUENCING VIRUS-, BACTERIA-, PARASITE-INFECTED CELLS AND/OR TUMOR CELLS AND METHOD FOR THE USE THEREOF

BACKGROUND OF THE INVENTION

The invention relates to biologically active molecules for influencing virus-, bacteria-, parasite-infected cells and/or tumor cells and a method for the use thereof. The aim of the invention is to influence virus-, bacteria-, parasite-infected cells and/or tumor cells physiologically, by means of one or more target proteases, even in the case of mutations of the target proteases.

The suggested biologically active molecules and the use thereof can be applied, in particular, for fighting and inhibiting the growth of abnormal cells, for example in tumor therapy and the treatment of virus infections, bacterial infections or infections with parasites.

The use of protease inhibitors in fighting virus infections was already described and has been applied for many years (for example EP 0691345 A3; U.S. Pat. No. 5,196,438 A; U.S. Pat. No. 5,541,206 A; U.S. Pat. No. 5,413,999 A; U.S. Pat. No. 5,484,926 A; U.S. Pat. No. 5,585,397 A).

The inhibition of the gene expression by introduction of short (19-23 bp), double-stranded RNA molecules (siRNA) or PNA molecules into eukaryotic cells, which is specific for a sequence segment of the mRNA of a target gene, was also described already (Elbashir S M et al.: Duplexes of 21-nucleotide RNAs mediate RNA interference in cultured mammalian cells, Nature, 2001 May 24, 411 (6836), 494-8; Liu Y et al.: Efficient and isoform-selective inhibition of cellular gene expression by peptide nucleic acids, Biochemistry, 2004 Feb. 24, 43(7), 1921-7; U.S. Pat. No. 5,898,031 A; U.S. Pat. No. 7,056,704 B2).

By means of such molecules, the reading of a gene and the production of an mRNA are not inhibited but in case of siRNA, a cell-intrinsic mechanism is initiated which degrades the target mRNA. Finally, as described earlier, the formation of a specific protein is suppressed without affecting the expression of further genes (post-transcriptional gene silencing).

For the suppression of the expression of a gene, siRNA and PNA molecules can be introduced directly into the cell by means of transfection reagents and electroporation (Zhang M et al.: Downregulation enhanced green fluorescence protein gene expression by RNA interference in mammalian cells, RNA Biol. 2004 May, 1(1), 74-7; Gilmore I R et al.: Delivery strategies for siRNA-mediated gene silencing, Epub 2004 May 22, Curr. Drug Deliv. 2006 April, 3(2), 147-5; U.S. Pat. No. 6,506,559 B1).

In this context, it is disadvantageous that siRNA is relatively instable, which can be improved by chemical modifications (U.S. Pat. No. 6,107,094 A).

Using biologically active molecules is particularly problematic for an application in vivo. For such application, possible methods were developed, for example stabilising siRNA molecules to reduce degradation (Morrissey et. al.: "Chemical Modifications of Synthetic siRNA", Pharmaceutical Discovery, May 1, 2005), and transfection reagents, for example nanoparticles, in vivo-jetPEI™, were developed, which introduce siRNA into cells also in vivo (Vernejoul et al.: Antitumor effect of in vivo somatostatin receptor subtype 2 gene transfer in primary and metastatic pancreatic cancer models, Cancer Research 62, 2002, 6124-31; Urban-Klein B, Werth S, Abuharbeid S, Czubayko F, Aigner A: RNAi-mediated gene-targeting through systemic application of poylethylenimine (PEI)-complexed siRNA in vivo, Gene Ther 12(5), 2005, 461-6).

Also, methods were developed wherein cells of a target tissue are increasingly transfected with siRNA in vivo (Ikeda et al.: "Ligand-Targeted Delivery of Therapeutic siRNA", Pharmaceutical Research, Vol. 23, No. 8, August 2006).

The administration of biologically active substances in vivo, however, is often problematic due to their systemic effect. The selective introduction of these substances into target cells does not take place in a sufficiently specific manner. This is disadvantageous, in particular with siRNA, PNA and RNA molecules which are to be effective in a selective manner and in target cells exclusively. By means of tissue- and cell-specifically marked transfection reagents (e.g. antibody/antigen-marked nanoparticles, TAT protein flanking, among others), no sufficient cell specificity is achieved. Consequently, mistransfections take place.

For the compensation of said mistransfections, a mechanism is known where the biological effect of siRNA, PNA and RNA molecules is inhibited by binding of peptides and these peptides are cleaved by means of target cell active enzymes for activating of siRNA, PNA and RNA in the target cells (WO 2008098569 A2).

A general problem in the application of protease inhibitors for the inhibition of infectivity or replication of viruses, bacteria or parasites and the growth of tumors is that the viral, bacterial, parasite or tumor-specific enzymes are modified slightly in a very rapid manner, for example by mutations, and thus the applied inhibitors have no effect any longer. In this way, viruses, bacteria, parasites or tumor cells can proliferate again despite inhibitors applied.

Due to the rapid mutation rate of the genetic material in virus-, bacteria- or parasite-infected cells or tumor cells, the use of siRNA, PNA and RNA molecules per se is not considered appropriate or sufficiently efficient, since modifications of the mRNA target sequence of the siRNA, PNA or RNA can also inhibit the intended application effect of the molecules used.

SUMMARY OF THE INVENTION

The problem underlying the invention is to effectively influence virus-, bacteria-, or parasite-infected cells and tumor cells in a targeted manner even in the case of mutations or modifications in the target protease.

According to the invention, for influencing virus-, bacteria- or parasite-infected cells and/or tumor cells biologically effective molecules are administered which consist of both at least one protease inhibitor for at least one specific target protease of the virus-, bacteria-, parasite-infested cells and/or tumor cells and at least one peptide-inhibited siRNA, PNA or RNA, the peptide bond of which is broken up by the at least one specific target protease for the purpose of activating the peptide-inhibited siRNA, PNA or RNA.

The protease inhibitor binds to the intended target protease of the virus-, bacteria-, parasite-infested cells and/or tumor cells in a manner known per se for the purpose of suppression of the biological or tumor activity of the cell. For the case that the administered protease inhibitor cannot bind to the target protease, for example due to a slight mutation of the target protease, and cannot inhibit said effect of the target protease as intended, (or in the case of residual activity of the target protease), the target protease has an effect on the peptide-inhibited siRNA, PNA or RNA, which is administered simultaneously with or sequentially, with a short time interval, to the protease inhibitor, the peptide bond of which has the same and/or a slightly modified protein sequence of the breaking site of the target protease for the purpose of breaking up the peptide bond by the target protease. Breaking up the peptide bond activates the effect of the siRNA, PNA or RNA, which then has an effect on the physiology of the cell and reduces the specific expression of the target gene. In this way, for example, the expression of a gene which is essential for the cell's viability is deactivated and, thus, the cell is killed. After their activation, the RNA, siRNA or PNA molecules interact with the mRNA of the target protease and in the case of siRNA, they form, together with special endoribonucleases, an RNA protein complex designated "RISC" (RNA induced silencing complex). The RISC complex binds to the target mRNA with endonucleases cutting the target mRNA. In this way, gene expression is prevented in a manner known per se and, thus, formation of target proteins is inhibited. When using activated PNA molecules, the binding to the target mRNA prevents translation.

Thus, it is achieved that, for example in the case of virus infections either the administered protease inhibitor binds to the specific target protease, inhibits it in an effective manner and, thus, replication of the virus is prevented, or, if said modification of the target protease (even it is only a very slight modification) does not (or no longer) allow linking of the protease inhibitor to the target protease (then the target protease would remain active or would be active again, so that replication of the virus is possible), then it is exactly this target protease (which could not be inhibited by the protease inhibitor) which activates said peptide-inhibited siRNA, PNA or RNA, which causes, for example, killing of the virus-infected cell. The same happens when the protease inhibitor does bind to the target protease but does not inhibit its effect completely so that there is a certain residual activity of the target protease, due to which virus replication could not be excluded.

For the treatment of HIV, which is presented in an exemplary manner, this means that the target protease of the HI virus is inhibited either in a direct manner by a protease inhibitor and, thus, leads to reduced replication or (it is known from experience that then HI virus mutants are selected the protease of which is not inhibited or only inhibited to a small extent by the protease inhibitor) the complementary mechanism of action starting form the siRNA, PNA or RNA mentioned is activated.

In this way the expression, for example, of genes which are essential for the viability of the cell could be reduced and apoptosis or necrosis processes could be triggered.

For example, small molecules, peptides, proteins, in particular antibodies, all of which are known per se, or chemical modifications thereof may be used as protease inhibitors.

Advantageously, the at least one protease inhibitor and the at least one peptide-inhibited siRNA, RNA or RNA, can be administered simultaneously in one molecule wherein the two of them are covalently bound.

However, it is also possible to administer the at least one protease inhibitor and the at least one peptide-inhibited siRNA in separate complexes which are not covalently bound simultaneously or sequentially with short time intervals.

The application of the biologically active molecules according to the invention can take place once or several times, wherein in the latter case, with further application the at least one protease inhibitor and the at least one peptide-inhibited siRNA, PNA or RNA, are used optionally having a modified effect on the virus-, bacteria-, parasite-infected cells and/or tumor cells due to concentration and/or molecular structure.

Depending on the application, the target protease, which is to be inhibited in its effect, can be a viral protease or a protease of a parasite or a bacterium. The peptide for the inhibition of the siRNA, RNA or PNA characterises the natural and modified form of the cutting site of the protease as breaking site, which is recognised by the protease and then broken up, in particular a cutting site which is also recognised and cut by a mutated form of the protease.

For the application of the biologically active molecules, it is also advantageous to administer them in combination with a transfection reagent, in particular lipids, polyethylene imines, nanoparticles, polymers, dextran.

In combination with the application of the at least one protease inhibitor and the at least one peptide-inhibited siRNA, PNA or RNA, further active agents can be administered which also influence the cellular properties of the virus-, bacteria-, parasite-infected cells and/or tumor cells or replication, infectivity, encapsulation or release of the virus, replication, infectivity, metabolism or release of a bacterium or a parasite.

The peptide-inhibited siRNA, RNA or PNA can be linked with further structures or functional elements, in particular for receptor-ligand systems, for Tat protein flanking, for the binding of aptamer complexes and for pegylation.

The invention, can be used for the treatment of virus-infected cells, parasite-infected cells, bacteria-infected cells and tumor cells.

BRIEF DESCRIPTION OF THE DRAWINGS

In the following, the invention is explained in detail by means of embodiments presented in the Figure.

The Figures show.

DETAILED DESCRIPTION OF THE INVENTION

Figure 1A:
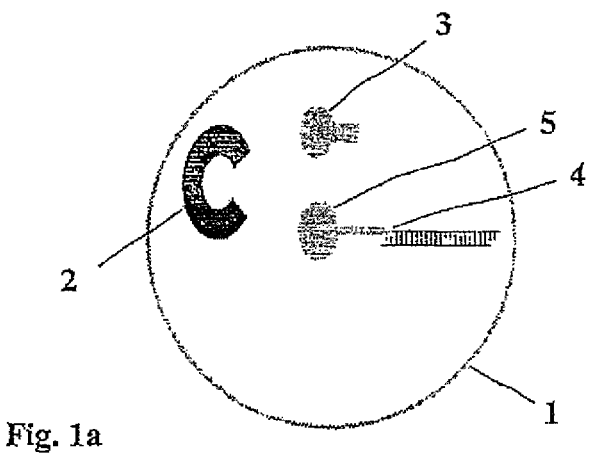
FIG. 1a-c: schematic diagram of alternative influencing of cells by introducing of biologically active molecules into the cells, consisting of one protease inhibitor and one peptide-inhibited siRNA.
  a): a cell with specific target protease to be inhibited and the biologically active molecules introduced (protease inhibitor and inactive peptide-inhibited siRNA)
  b): physiological influencing of the cell by the protease inhibitor
  c): physiological influencing of the cell by the activated siRNA

In FIG. 1a, a virus-infected cell 1 with target protease 2, which is to be inhibited, is presented. According to the invention, a biologically active molecule, is added to the virus-infected cell 1, wherein the biologically active molecule consists of a protease inhibitor 3 for target protease 2, which is known per se, for example Invirase, Norvir, Pentothal, Amprenavir or Viracept for HIV infections, and a peptide-inhibited siRNA 5, which is also known per se, and which is inactive due to a peptide bond 4. Peptide bond 4 of the peptide-inhibited siRNA 5 can be broken up for the purpose of its activation by target protease 2, wherein the protein sequence of peptide bond 4 at the cutting site corresponds to the exact or slightly modified target protease sequence.

Figure 1B:
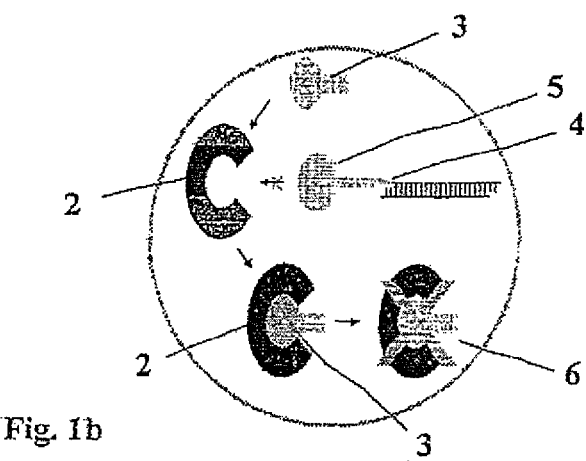

FIG. 1*b* schematically shows how protease inhibitor 3 binds to and effectively inhibits target protease 2 as intended. In this case the peptide bond 4 of the peptide-inhibited siRNA 5 is not broken up by target protease 2 and the target protease 2, which is inactivated in its damaging effect, is converted into protease 6, which is inhibited with regard to this effect. The peptide-inhibited siRNA 5 remains in cell 1 without effect.

Figure 1C:
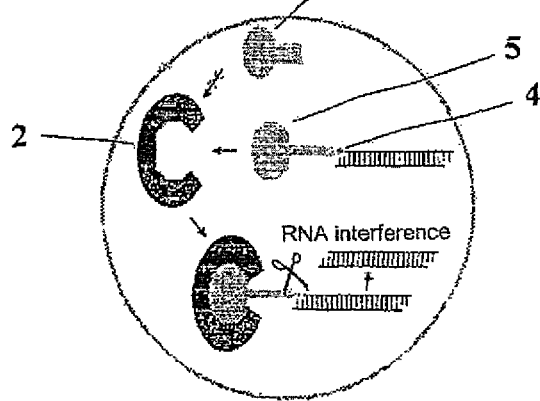
Figure 2:
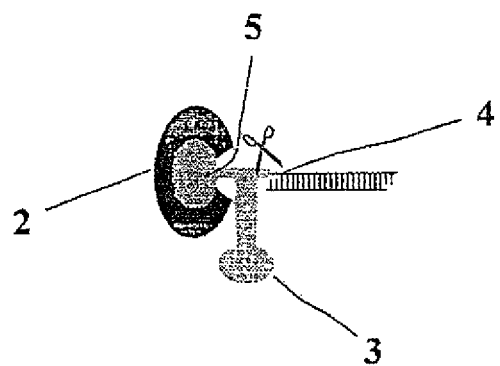
FIG. 2: biologically active molecules with covalent bond between the protease inhibitor and the peptide-inhibited siRNA.
Figure 3:
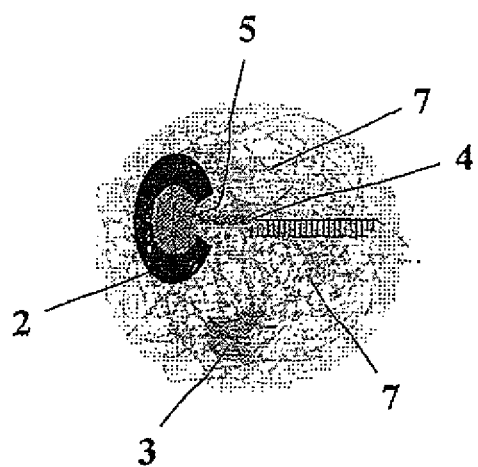
FIG. 3: biologically active molecules with non-covalent bond between the protease inhibitor and the peptide-inhibited siRNA and administration in a complex, for example a transfection system

For the case that protease inhibitor 3 cannot bind or cannot bind completely to target protease 2 and cannot inhibit it or its damaging effect completely (for example by a slight mutation), target protease 2 still has at least a certain residual activity by means of which it is able to break up said peptide bond 4 of the peptide-inhibited siRNA 5. In this case, FIG. 1*c* shows how peptide-inhibited siRNA 5, rather than protease inhibitor 3, binds to the target protease 2. Due to the cutting of the peptide bond 4, which is symbolically illustrated, for example, the expression of a gene essential for the viability of cell 1 can be inhibited by means of the now activated siRNA, and cell 1 dies.

The biologically active molecules to be introduced into cell 1 for it to be physiologically affected, in particular for the purpose of combined administration, can have a covalent bond between protease inhibitor 3 and the peptide-inhibited siRNA 5 with peptide bond 4 (cf. FIG. 2). In this context, the bond is sterically designed in such a way that protease inhibitor 3 can bind to and inhibit target protease 2. In case of a possible inactivity of the protease inhibitor or activity of the target protease which is not inhibited or not inhibited completely (cf. FIG. 1*c*), the peptide inhibiting siRNA 5 is cleaved from siRNA 5 together with protease inhibitor 3 for the purpose of its activation in the manner described.

The biologically active molecules can also be used in a complex 7, for example of polyetheleneimine, dextran or polyethylene glycol (cf. FIG. 3). In this context, such complex in particular serves as a transfection system, which is not explicitly illustrated, for the purpose of introduction into cells and/or stabilisation of protease inhibitor 3 and peptide-inhibited siRNA 5. Furthermore, in FIG. 3, protease inhibitor 3 and peptide-inhibited siRNA 5 having a non-covalent bond are illustrated. Moreover, a non-covalent bond allows for separate and possibly sequential application of the molecule components.

The use of the biologically active molecules in combination with said complex 7 can, however, also take place with a covalent bond between protease inhibitor 3 and peptide-inhibited siRNA 5.

The invention claimed is:

1. A composition comprising a biologically active molecule for influencing virus-, bacteria-, or parasite-infected cells and/or tumor cells, comprising a protease inhibitor for a specific target protease of the virus-, bacteria-, or parasite-infected cells and/or tumor cells and a siRNA, PNA or RNA inhibited by a peptide having a peptide bond shared with the siRNA, PNA or RNA, the peptide bond providing a breaking site, wherein the peptide bond has a protein sequence that is preselected to be slightly modified with regard to a protein sequence of a breaking site of the specific target protease, the preselected protein sequence of the peptide bond being provided for the purpose of activating the peptide-inhibited siRNA, PNA or RNA when the peptide bond shared with the siRNA, PNA or RNA is broken at the breaking site by the specific target protease when the protease inhibitor cannot bind or cannot effectively bind to the specific target protease.

2. The composition according to claim 1, wherein the protease inhibitor and the peptide-inhibited siRNA, PNA or RNA are combined in one molecule and are covalently bound therein.

3. The composition according to claim 1, wherein the peptide-inhibited siRNA, PNA or RNA further comprises linkage to a receptor-ligand system, Tat protein flanking, binding of aptamer complexes or pegylation.

4. A method for influencing virus-, bacteria-, or parasite-infected cells and/or tumor cells, comprising administering to the cells the composition of claim 1.

5. The method according to claim 4, wherein the protease inhibitor and the peptide-inhibited siRNA, PNA or RNA are administered in combination with a transfection reagent.

6. The method according to claim 4, wherein the administration of the composition comprising the protease inhibitor and the peptide-inhibited siRNA, PNA or RNA will also influence cellular properties of the virus-, bacteria-, or parasite-infected cells and/or tumor cells or replication, infectivity, encapsulation or release of the virus or replication, infectivity, metabolism or release of the bacteria or a parasite.

7. The method according to claim 4, wherein the protease inhibitor and the peptide-inhibited siRNA, PNA or RNA are combined in one molecule and are covalently bound therein.

8. The method according to claim 5, wherein the transfection agent is selected from the group consisting of lipids, polyethyleneimines, dextrane, nanoparticles and polymers.

9. A biologically active molecule for influencing virus-, bacteria-, or parasite-infected cells and/or tumor cells, comprising a protease inhibitor for a specific target protease of the virus-, bacteria-, or parasite-infected cells and/or tumor cells, and further comprising a peptide-inhibited siRNA, PNA or RNA which is activated by the specific target protease breaking a peptide bond of the peptide-inhibited siRNA, PNA or RNA, wherein the protease inhibitor and the peptide-inhibited siRNA, PNA or RNA are combined in one molecule and are covalently bound therein.

* * * * *